(12) United States Patent
Green et al.

(10) Patent No.: US 6,593,291 B1
(45) Date of Patent: *Jul. 15, 2003

(54) COMPOSITIONS AND METHODS OF USE OF LIGANDS THAT BIND COMPONENTS OF THE BLOOD COAGULATION/CLOTTING PATHWAY FOR THE TREATMENT OF CANCER AND ANGIOGENIC-BASED DISEASE

(75) Inventors: Shawn J. Green, Vienna, VA (US); Adonia E. Papathanassiu, Silver Spring, MD (US)

(73) Assignee: EntreMed, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/418,546

(22) Filed: Oct. 14, 1999

Related U.S. Application Data

(63) Continuation-in-part of application No. 08/796,850, filed on Feb. 6, 1997, now Pat. No. 5,981,471.

(51) Int. Cl.[7] ................................................ A01N 37/18
(52) U.S. Cl. ........................ 514/2; 514/21; 435/7.1; 530/350; 530/300
(58) Field of Search .......................... 435/7.1; 530/350, 530/300; 514/2, 21

(56) References Cited

U.S. PATENT DOCUMENTS

| | | | |
|---|---|---|---|
| 5,629,327 A | 5/1997 | D'Amato | 514/323 |
| 5,639,725 A | 6/1997 | O'Reilly et al. | 514/12 |
| 5,733,876 A | 3/1998 | O'Reilly et al. | 514/12 |
| 5,792,845 A | 8/1998 | O'Reilly et al. | 536/23.1 |
| 5,854,205 A | 12/1998 | O'Reilly et al. | 514/2 |

FOREIGN PATENT DOCUMENTS

| | | | |
|---|---|---|---|
| WO | WO 94/04178 | * | 3/1994 |
| WO | WO 98/34634 | * | 8/1998 |

OTHER PUBLICATIONS

Donnelly et al., *Ancylostoma caninum Anticoagulant Peptide Blocks Metastasis In Vivo and Inhibits Factor Xa Binding to Melanoma Cells In Vitro*, Schattauer Verlag, Stuttgart, Thromb. Haemost. 1998; 79; 1041–7.

Bach, *Initiation of Coagulation by Tissue Factor*, CRC Crit. Rev. Biochem. vol. 23, Issue 4, pp. 339–368 (1988).

Balian et al., *Structure of Rat Skin Collagen 1–CB8. Amino Acid Sequence of the Hydroxylaminie–Produced Fragment HA2*, Biochemistry 11(20):3798–3806 (1972).

Hanahan et al., *Patterns and Emerging Mechanisms of the Angiogenic Switch during Tumorgenesis*, Cell, vol. 86, pp. 353–364, (1996).

Kasza et al., *Specificity of serine proteinase/serpin complex binding to very–low–density liproprotein receptor and $_2$–macroglobin receptor/low–density–lipoprotein–receptor–related–protein*, Eur. J. Biochem. 248: 270–271 (1997).

Long et al., *Human Protein S Cleavage and Inactivation by Coagulation Factor Xa*, J. Biol. Chem., vol. 273, No. 19, Issue of May 8, pp. 11521–11526 (1998).

Mounier et al., *Inhibition of Prothrombinase by Human Secretory Phosphilpase Az Involves Binding to Factor Xa*, J. Biol. Chem., vol. 273, No. 37, Issue Sep. 11, pp. 23764–23772 (1998).

Rezaie, *Rapid Activation of Protein C by Factor Xa and Thrombin in the Presence of Polyanionic Compounds*, Blood, vol. 91, No. 12, pp. 4572–4580 (1998).

\* cited by examiner

Primary Examiner—Christopher S. F. Low
Assistant Examiner—Hope A. Robinson
(74) Attorney, Agent, or Firm—Kilpatrick Stockton LLP

(57) ABSTRACT

Compositions and methods effective in inhibiting abnormal or undesirable cell proliferation, particularly endothelial cell proliferation and angiogenesis related to neovascularization and tumor growth are provided. The compositions comprise naturally occurring, or synthetic proteins, peptides, or protein fragments capable of binding to components of the blood coagulation pathway. The compositions may be administered using a pharmaceutically acceptable carrier. The methods involve administering to a human or animal the composition described herein in a dosage sufficient to inhibit cell proliferation, particularly endothelial cell proliferation. The methods are useful for treating diseases and processes mediated by undesired and uncontrolled cell proliferation, such as cancer, particularly by inhibiting angiogenesis. Administration of the composition to a human or animal having prevascularized metastasized tumors is useful for preventing the growth or expansion of such tumors.

22 Claims, 10 Drawing Sheets

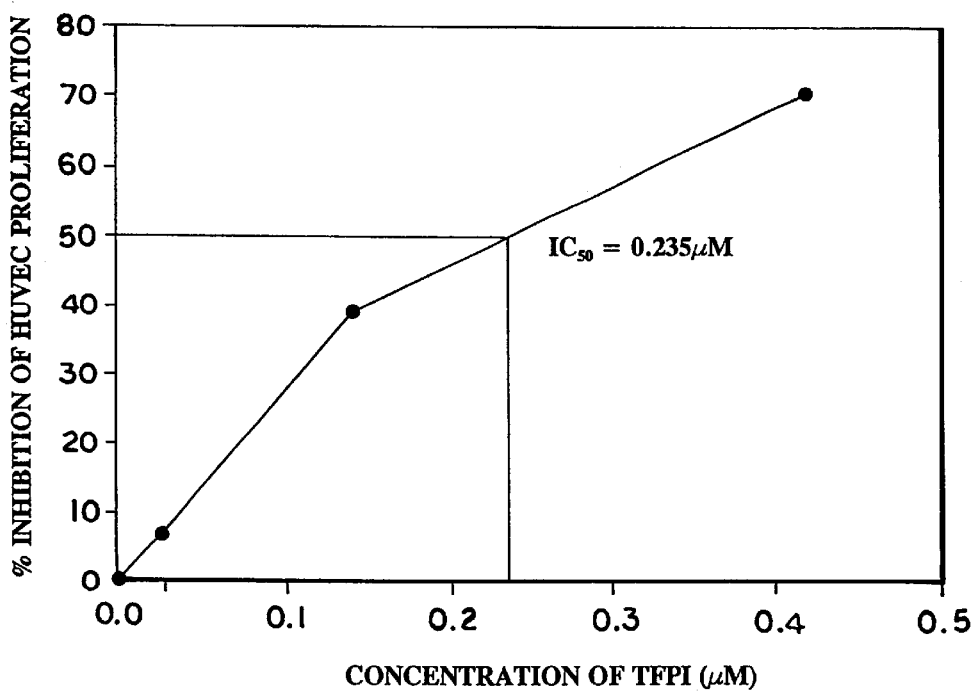
Fig_1A
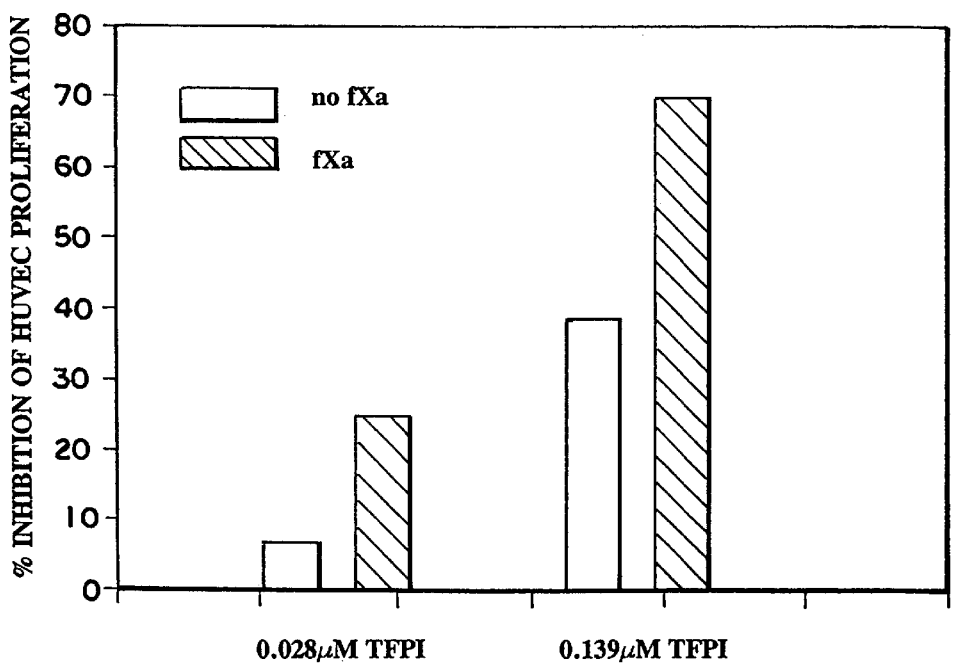
Fig_1B

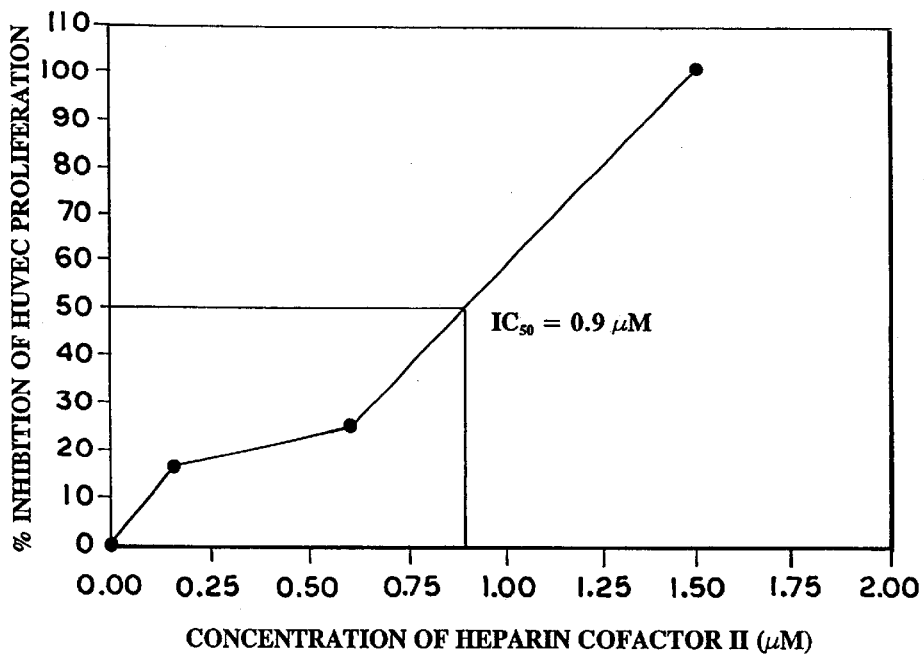
FIG._2A
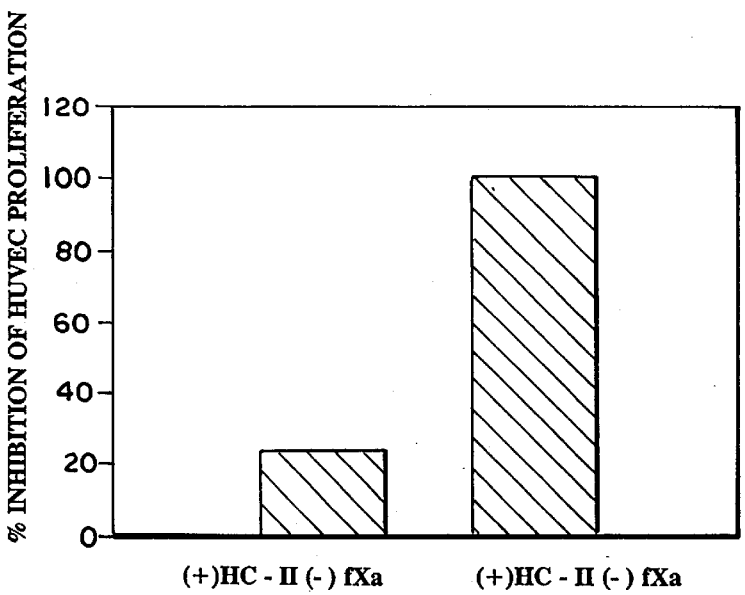
FIG._2B

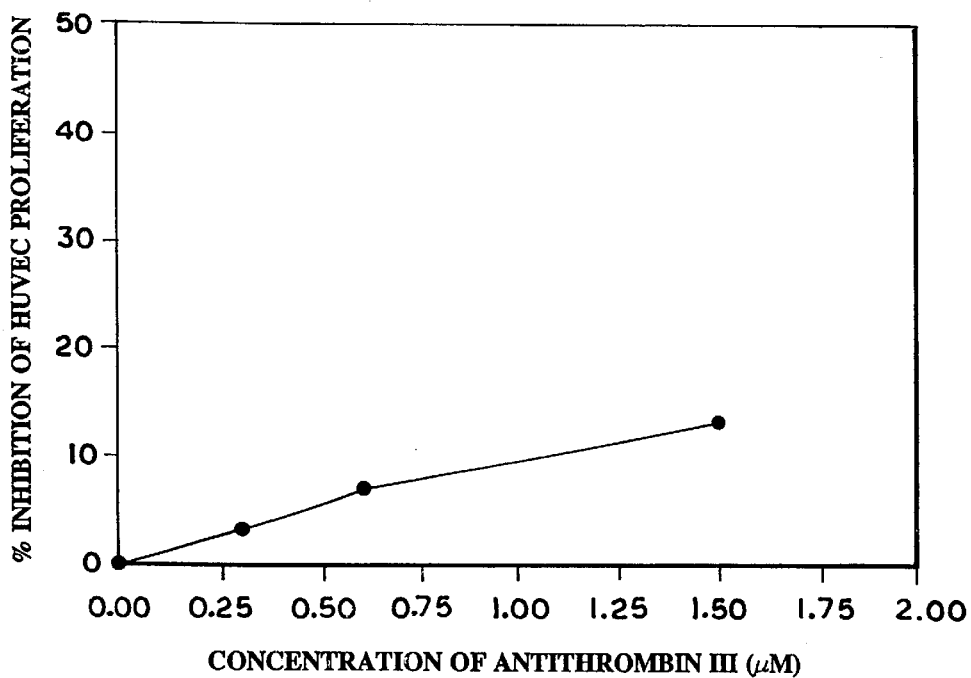
Fig_4A
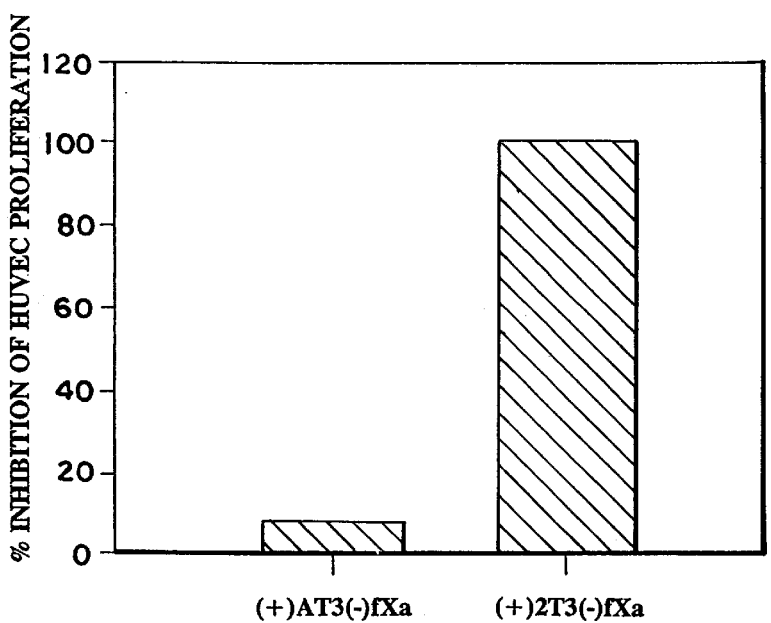
Fig_4B

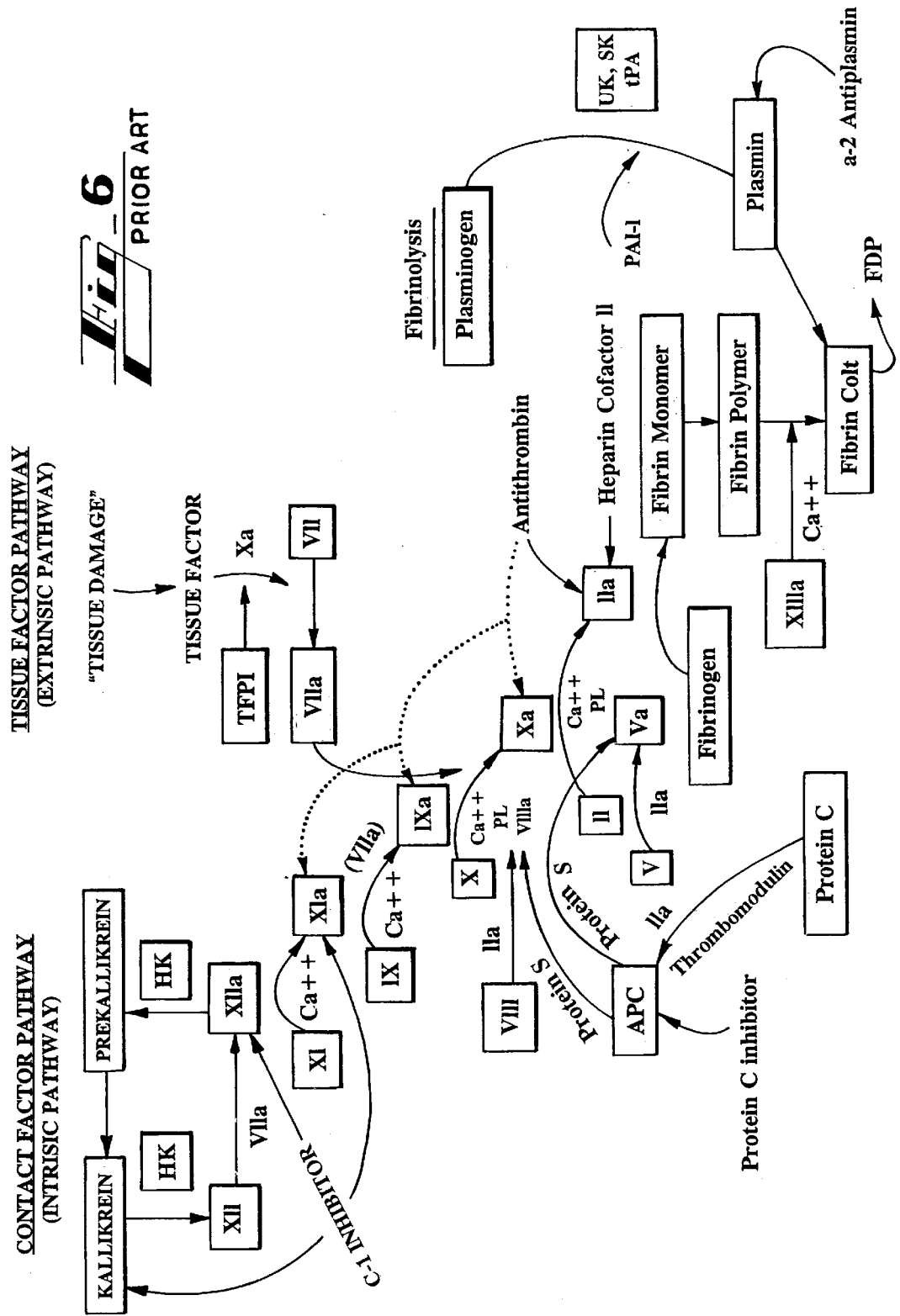
FIG_6 PRIOR ART

COMPOSITIONS AND METHODS OF USE OF LIGANDS THAT BIND COMPONENTS OF THE BLOOD COAGULATION/CLOTTING PATHWAY FOR THE TREATMENT OF CANCER AND ANGIOGENIC-BASED DISEASE

The present application is a continuation-in-part application of U.S. patent application Ser. No. 08/796,850, filed Feb. 6, 1997, now U.S. Pat. No. 5,981,471.

FIELD OF THE INVENTION

The present invention relates to compositions and methods for the inhibition of cellular proliferation. More particularly, the present invention relates to the use of ligands that bind to components of the blood coagulation/clotting pathway, and inhibit angiogenesis and angiogenesis-related diseases.

BACKGROUND OF THE INVENTION

Cellular proliferation is a normal ongoing process in all living organisms and is one that involves numerous factors and signals that are delicately balanced to maintain regular cellular cycles. The general process of cell division is one that consists of two sequential processes: nuclear division (mitosis), and cytoplasmic division (cytokinesis). Because organisms are continually growing and replacing cells, cellular proliferation is a central process that is vital to the normal functioning of almost all biological processes. Whether or not mammalian cells will grow and divide is determined by a variety of feedback control mechanisms, which include the availability of space in which a cell can grow, and the secretion of specific stimulatory and inhibitory factors in the immediate environment.

When normal cellular proliferation is disturbed or somehow disrupted, the results can affect an array of biological functions. Disruption of proliferation could be due to a myriad of factors such as the absence or overabundance of various signaling chemicals or presence of altered environments. Some disorders characterized by abnormal cellular proliferation include cancer, abnormal development of embryos, improper formation of the corpus luteum, difficulty in wound healing as well as malfunctioning of inflammatory and immune responses.

Cancer is characterized by abnormal cellular proliferation. Cancer cells exhibit a number of properties that make them dangerous to the host, often including an ability to invade other tissues and to induce capillary ingrowth, which assures that the proliferating cancer cells have an adequate supply of blood. One of the defining features of cancer cells is that they respond abnormally to control mechanisms that regulate the division of normal cells and continue to divide in a relatively uncontrolled fashion until they kill the host.

Angiogenesis and angiogenesis-related diseases are closely affected by cellular proliferation. As used herein, the term "angiogenesis" means the generation of new blood vessels into a tissue or organ. Under normal physiological conditions, humans or animals undergo angiogenesis only in very specific restricted situations. For example, angiogenesis is normally observed in wound healing, fetal and embryonal development and formation of the corpus luteum, endometrium and placenta. The term "endothelium" is defined herein as a thin layer of flat cells that lines serous cavities, lymph vessels, and blood vessels. These cells are defined herein as "endothelial cells". The term "endothelial inhibiting activity" means the capability of a molecule to inhibit angiogenesis in general. The inhibition of endothelial cell proliferation also results in an inhibition of angiogenesis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent, unregulated angiogenesis occurs in a multiplicity of disease states, tumor metastasis and abnormal growth by endothelial cells and supports the pathological damage seen in these conditions. The diverse pathological disease states in which unregulated angiogenesis is present have been grouped together as angiogenic-dependent, angiogenic-associated, or angiogenic-related diseases. These diseases are a result of abnormal or undesirable cell proliferation, particularly endothelial cell proliferation.

The hypothesis that tumor growth is angiogenesis-dependent was first proposed in 1971 by Judah Folkman (*N. Engl. Jour. Med.* 285:1182 1186, 1971). In its simplest terms the hypothesis proposes that once tumor "take" has occurred, every increase in tumor cell population must be preceded by an increase in new capillaries converging on the tumor. Tumor "take" is currently understood to indicate a prevascular phase of tumor growth in which a population of tumor cells occupying a few cubic millimeters volume and not exceeding a few million cells, survives on existing host microvessels. Expansion of tumor volume beyond this phase requires the induction of new capillary blood vessels. For example, pulmonary micrometastases in the early prevascular phase in mice would be undetectable except by high power microscopy on histological sections. Further indirect evidence supporting the concept that tumor growth is angiogenesis dependent is found in U.S. Pat. Nos. 5,639,725, 5,629,327, 5,792,845, 5,733,876, and 5,854,205, all of which are incorporated herein by reference.

Thus, it is clear that cellular proliferation, particularly endothelial cell proliferation, and most particularly angiogenesis, plays a major role in the metastasis of a cancer. If this abnormal or undesirable proliferation activity could be repressed, inhibited, or eliminated, then the tumor, although present, would not grow. In the disease state, prevention of abnormal or undesirable cellular proliferation and angiogenesis could avert the damage caused by the invasion of the new microvascular system. Therapies directed at control of the cellular proliferative processes could lead to the abrogation or mitigation of these diseases.

What is needed are compositions and methods which can inhibit abnormal or undesirable cellular proliferation, especially the growth of blood vessels into tumors. The compositions should be able to overcome the activity of endogenous growth factors in premetastatic tumors and prevent the formation of the capillaries in the tumors thereby inhibiting the development of disease and the growth of tumors. The compositions should also be able to modulate the formation of capillaries in angiogenic processes, such as wound healing and reproduction. Finally, the compositions and methods for inhibiting cellular proliferation should preferably be non-toxic and produce few side effects.

SUMMARY OF THE INVENTION

Compositions and methods are provided that are effective in inhibiting abnormal or undesirable cell proliferation, particularly endothelial cell proliferation and angiogenesis related to neovascularization and tumor growth. The compositions comprise naturally occurring or synthetic proteins, peptides, or protein fragments containing all, or active fragments of ligands that bind components of the blood coagulation/clotting pathway, optionally provided in a pharmaceutically acceptable carrier.

Representative ligands useful for the present invention comprise proteins or peptides that bind components of both the intrinsic and extrinsic blood clotting pathways such tissue factor (TF), and/or TF cofactor complexes, factor V, factor VIII, factor XII, factor XI, factor X, factor IX, factor VIIa, thrombin, fibrinogen and fibrin.

Preferred ligand compositions of the present invention, include but are not limited to, proteins comprising Kunitz domain proteins, non-Kunitz domain proteins, Kringle-rich proteins, TF cofactors (i.e. factor VIIa, phospholipids, gangliosides), TF antagonists (i.e. antibodies), and any other molecules that bind TF. More particularly, the compositions of the present invention comprise TFPI, protein S, protein Z, protein Z inhibitor, protein C, activated protein C, protein C inhibitor, prothrombin, group II secretory phospholipase A2, complement protein C4b, protease nexin-1, beta2-glycoprotein I, and serpins anticoagulants such as antithrombin and heparin cofactor II.

Preferably, the protein, peptide or protein fragment contains all or an active portion of the above identified proteins. The term "active fragment", as used herein, means a portion of a protein that inhibits abnormal or undesirable cell proliferation, more specifically inhibits endothelial cell proliferation. Also included in the present invention are homologs, peptides, or protein fragments, or combinations thereof of the above-identified proteins, that inhibit abnormal or undesirable cell proliferation. Most preferably, the protein or peptide comprises TF or factor Xa binding ligand, or an active fragment thereof.

Though not wishing to be bound by the following theory, it is believed that by inhibiting endothelial cell proliferation, the methods and compositions described herein are useful for inhibiting tumor growth and metastasis by blocking tumor vascularization. The methods provided herein for treating diseases and processes mediated by undesired and uncontrolled cell proliferation, such as cancer, involve administering to a human or animal the composition described herein in a dosage sufficient to inhibit cell proliferation, particularly endothelial cell proliferation. The methods are especially useful for treating or repressing the growth of tumors, particularly by inhibiting angiogenesis. Administration of the compositions to a human or animal having prevascularized metastasized tumors is useful for preventing the growth or expansion of such tumors.

Accordingly, it is an object of the present invention to provide methods and compositions for treating diseases and processes that are mediated by abnormal or undesirable cellular proliferation.

It is another object of the present invention to provide methods and compositions for treating or repressing the growth of a cancer.

It is yet another object of the present invention to provide methods and compositions for therapy of cancer that has minimal side effects.

It is another object of the present invention to provide methods and compositions for treating diseases and processes that are mediated by angiogenesis.

Yet another object of the present invention is to provide methods and compositions comprising the use of proteins, peptides, active fragments and homologs thereof that inhibit endothelial cell proliferation.

Another object of the present invention is to provide methods and compositions for treating diseases and processes that are mediated by angiogenesis by administrating antiangiogenic compounds comprising ligands that bind components of the blood coagulation/clotting pathway.

It is another object of the present invention to provide methods and compositions for treating diseases and processes that are mediated by angiogenesis by administrating antiangiogenic compounds comprising ligands that bind components of the intrinsic and/or extrinsic blood clotting pathways wherein in such components comprise tissue factor (TF), and/or TF cofactor complexes, factor V, factor VIII, factor XII, factor XI, factor X, factor IX, factor VIIa, thrombin, fibrinogen and fibrin.

It is a further object of the present invention to provide methods and compositions for treating diseases and processes that are mediated by angiogenesis by administrating antiangiogenic compounds comprising ligands, wherein the ligands comprise Kunitz domain proteins, non-Kunitz domain proteins, Kringle-rich proteins, TF cofactors, TF antagonists, factor VIIa antagonists or inhibitors and factor Xa antagonists or inhibitors.

It is another object of the present invention to provide methods and compositions for treating diseases and processes that are mediated by angiogenesis comprising administration of antiangiogenic compounds comprising TFPI, protein S, protein Z, protein Z inhibitor, protein C, activated protein C, protein C inhibitor, prothrombin, group II secretory phospholipase A2, complement protein C4b, protease nexin-1, beta2-glycoprotein I, and serpins anticoagulants (such as antithrombin and heparin cofactor II) and inhibitors of factors TF, TF/VIIa, VIIa, Xa.

It is still another object of the present invention to provide antiangiogenic compositions comprising ligands that bind components of the intrinsic and extrinsic blood clotting pathways wherein the compositions further comprise pharmaceutically acceptable carriers.

Yet another object of the present invention is to provide antiangiogenic compositions comprising ligands that bind components of the intrinsic and/or extrinsic blood clotting pathways wherein the compositions further comprise pharmaceutically acceptable carriers that may be administered intramuscularly, intravenously, transdermally, orally, or subcutaneously.

It is yet another object of the present invention to provide compositions and methods for treating diseases and processes that are mediated by angiogenesis including, but not limited to, hemangioma, solid tumors, blood borne tumors, leukemia, metastasis, telangiectasia, psoriasis, scleroderma, pyogenic granuloma, myocardial angiogenesis, Crohn's disease, plaque neovascularization, arteriovenous malformations, corneal diseases, rubeosis, neovascular glaucoma, diabetic retinopathy, retrolental fibroplasia, arthritis, diabetic neovascularization, macular degeneration, wound healing, peptic ulcer, Helicobacter related diseases, fractures, keloids, vasculogenesis, hematopoiesis, ovulation, menstruation, placentation, and cat scratch fever.

These and other objects, features and advantages of the present invention will become apparent after a review of the following detailed description of the disclosed embodiment and the appended claims.

BRIEF DESCRIPTION OF THE FIGURES

FIG. 1A is a graph showing inhibition of bFGF-induced proliferation of HUVEC cells by TFPI.

FIG. 1B is a graph showing increased antiproliferative activity of 0.028 μM and 0.139 μM TFPI with factor Xa (fXa) in the presence of phospholipids.

FIG. 2A is a graph showing inhibition of bFGF-induced proliferation of HUVEC cells by Heparin Cofactor II (HC-II).

FIG. 2B is a graph showing increased antiproliferative activity of HC-II following preincubation of 0.6 μM HC-II with fXa in the presence of phospholipids.

FIG. 4A is a graph showing inhibition of bFGF-induced proliferation of HUVEC cells by Antithrombin III (AT3).

FIG. 4B is a graph showing increased antiproliferative activity of AT3 following preincubation of 0.6 μM AT3 with fXa in the presence of phospholipids.

FIG. 6 is a schematic diagram showing the various components of the intrinsic and extrinsic pathways of the blood clotting/coagulation system. (Prior Art)

DETAILED DESCRIPTION

Figure 1C:
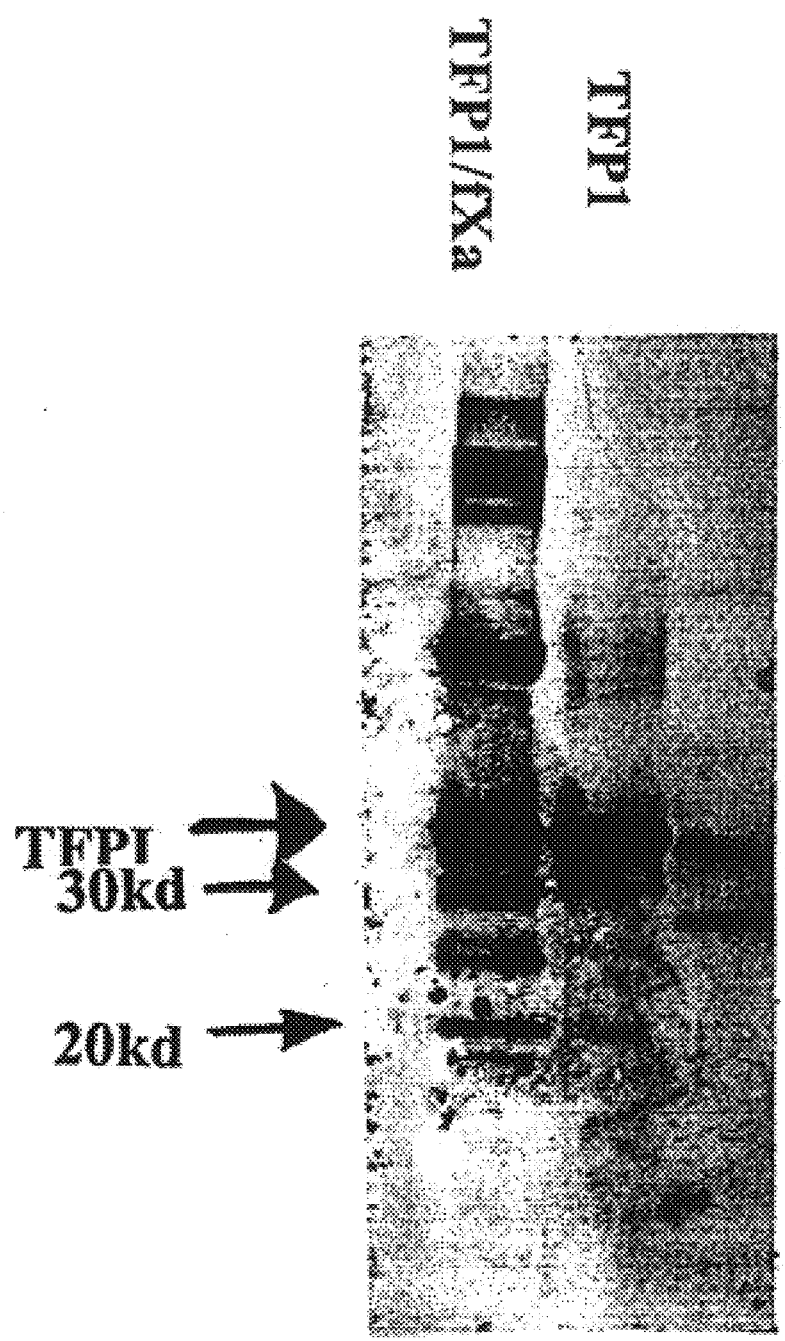
FIG. 1C is a representation of the results of an SDS-PAGE mobility/Immunoblotting analysis of the mixture TFPI/factor Xa/phospholipids showing that fXa partially cleaves TFPI to fragments with approximate MW 30 Kd and 20 Kd.

The following description includes the best presently contemplated mode of carrying out the invention. This description is made for the purpose of illustrating the general principles of the invention and should not be taken in a limiting sense. The entire text of the references mentioned herein are hereby incorporated in their entireties by reference, including U.S. patent application Ser. No. 09/130,273, filed Aug. 6, 1998; and U.S. patent application Ser. No. 08/796,850, filed Feb. 6, 1997.

Tissue Factor (TF) is a 45 Kd transmembrane glycoprotein that consists of a 219-amino acid extracellular domain, a 23-amino acid transmembrane region, and a 21-amino acid intracellular domain (see Bach, *CRC Crit. Rev. Biochem.* 23:339 (1988). TF binds and allosterically activates factor VIIa (fVIIa) and the complex TF/fVIIa is responsible for thrombin generation via activation of factors IX and X and is the major initiator of blood clotting under physiological conditions. TF has been localized in a variety of tumor and host cells. TF expression is induced by a variety of proinflammatory cytokines, and although it is not synthesized by cells within the vasculature, such as monocytes and endothelial cells, expression is ensured following vascular injury that initiates activation of the blood coagulation cascade. Accordingly it is thought that inflammation, blood coagulation, and blood vessel formation are interdependent processes and that such processes play an essential role in hematogenous metastasis.

Studies with various experimental metastatic tumor models have shown that, in order to metastasize, tumor cells need to migrate from the site of primary tumor into the blood circulation, travel to a distant target organ, arrest in the microvasculature, extravasate, and grow at the secondary site. In this multistep process, thrombin generation and fibrin formation appear to play important roles. Though not wishing to be bound by the following theory, it is believed that since a majority of the cancer cells that successfully enter the circulation are rapidly eliminated due to blood turbulence, in order to enhance survival, tumor cells tend to aggregate with each other or host cells such as platelets and lymphocytes. They form multicellular emboli (also called thrombi) that are often coated with fibrin. It is thought that these thrombi protect tumor cells against mechanical forces and stabilize the interaction of tumor cells with the microvasculature of the target organ. In addition, thrombin generation on the surface of the tumor cells assists in extravasation by inducing vasodilation of the endothelial cells of the microvasculature, degradation of endothelial cell matrix, and expression of cell-cell adhesion molecules such as intercellular adhesion molecule 1, P-, and E-selectins on the surface of endothelial cells.

The inventors of the present invention have discovered unique compositions and methods for the treatment of diseases and processes that are mediated by, or associated with, abnormal or undesirable cellular proliferation. The compositions comprise isolated naturally occurring or synthetic proteins, peptides, or protein fragments, containing all or an active fragment of ligands that bind components of the intrinsic or extrinsic blood coagulation/clotting pathways, including but not limited to, tissue factor (TF), factor V, factor Va, factor VIIa, factor VIII, factor VIIIa, factor IX, factor IXa, factor X, factor Xa, factor XI, factor XIa, factor XII, factor XIIa, thrombin, fibrinogen, fibrin,TF cofactor complexes, factor VIIIa complexes, factor Xa complexes, TF/VIIa complexes, factor Xa/Protein Z complexes, factor Xa/factor Va complexes, factor IXa/factor VIII complexes, factor VIIa multicomplexes, factor Xa multicomplexes, and prothrombinase complexes. In addition, the present invention comprises molecules and compounds that effect expression of blood clotting components, and further comprises antibodies and other molecules related to the components. Preferably, the compositions of the present invention comprise naturally occurring or synthetic ligands that bind TF. For delivery to a human or animal, the compositions may optionally comprise a pharmaceutically acceptable carrier or synthetic ligands that bind TF, factors VII and Xa, or their complexes such as prothrombinase complex, complex TF/fVIIa or complex fXa/Protein Z.

Preferably, the ligand compositions of the present invention, include but are not limited to, proteins comprising Kunitz domain proteins, non-Kunitz domain proteins, Kringle-rich proteins, TF cofactors (i.e. factor VIIa, phospholipids, gangliosides), TF antagonists (i.e. antibodies), active fragments thereof, and any other molecules that bind TF. More particularly, the compositions of the present invention may comprise TFPI (binds to factor Xa and complex TF/VIIa), antithrombin (binds to fXa and complex TF/VIIa), prothrombin (binds to factor Xa), heparin cofactor II (binds to thrombin and factor Xa), anticoagulant protein S (binds to factor Xa and factor V), protein C (binds to factor Xa, thrombin), activated protein C (binds to factor V, factor VIII), protein C inhibitor (binds to fXa, thrombin), protein Z (binds to factor Xa), protein Z inhibitor (binds to complex factor Xa/protein Z), tick anticoagulant peptide (binds to factor Xa), protease nexin-1 (binds to factor Xa), beta2-glycoprotein I (binds to factor Xa), complement protein C4b (binds to factor Xa), and group II secretory phospholipase A2 (binds to factor Xa).

The term "active fragment" is defined herein as the antiproliferative portion of a ligand or molecule necessary for binding a component in the blood coagulation/clotting pathway, preferably tissue factor. The active fragment has the ability to inhibit endothelial cell proliferation by in vivo or in vitro assays or other known techniques.

As noted above, the compositions of the present invention may be optionally combined with a pharmaceutical carrier. The term "carrier" as used herein comprises delivery mechanisms known to those skilled in the art including, but not limited to, keyhole-limpet hemocyanin (KLH), bovine serum albumin (BSA) and other adjuvants. It is to be understood that the ligand compositions of the present invention can further comprise adjuvants, preservatives, diluents, emulsifiers, stabilizers, and other components that are known and used for pharmaceutical compositions of the prior art. Any adjuvant system known in the art can be used for the compositions of the present invention. Such adjuvants include, but are not limited to, Freund's incomplete adjuvant, Freund's complete adjuvant, polydispersed β-(1,4) linked acetylated mannan ("Acemannan"), TITERMAX® (polyoxyethylene-polyoxypropylene copolymer adjuvants from CytRx Corporation (Norcross, Ga.), modified lipid adjuvants from Chiron Corporation (Emeryville, Calif.), saponin derivative adjuvants from Aguila Biopharmaceuticals (Worcester, Mass.), killed *Bordetella pertussis*, the lipopolysaccharide (LPS) of gram-negative bacteria, large polymeric anions such as dextran sulfate, and inorganic gels such as alum, aluminum hydroxide, or aluminum phosphate, ovalbumin; flagellin; thyroglobulin; serum albumin of any species; gamma globulin of any species; and polymers of D- and/or L-amino acids.

In accordance with the methods of the present invention, the compositions described herein, comprising proteins, peptides, or protein fragments comprising all, or an active fragment of a ligand that binds a blood clotting component, optionally in a pharmaceutically acceptable carrier, is administered to a human or animal exhibiting undesirable cell proliferation in an amount sufficient to inhibit the undesirable cell proliferation, particularly endothelial cell proliferation, angiogenesis or an angiogenesis-related disease, such as cancer.

Definitions

The terms "a", "an" and "the" as used herein are defined to mean one or more and include the plural unless the context is inappropriate.

As used herein the term "blood coagulation factor" is defined to mean an active enzyme and/or its zymogen counterpart. For example, a blood coagulation factor comprises the ligand factor Xa, and also binds to its zymogen counterpart, factor X.

The term "peptides," are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the peptide, or to the alpha-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide.

Typically, the amino acids making up a peptide are numbered in order, starting at the amino terminal and increasing in the direction toward the carboxy terminal of the peptide. Thus, when one amino acid is said to "follow" another, that amino acid is positioned closer to the carboxy terminal of the peptide than the preceding amino acid.

The term "residue" is used herein to refer to an amino acid (D or L) that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

The phrase "consisting essentially of" is used herein to exclude any elements that would substantially alter the essential properties of the peptides to which the phrase refers. Thus, the description of a peptide "consisting essentially of . . . " excludes any amino acid substitutions, additions, or deletions that would substantially alter the biological activity of that peptide.

Furthermore, one of skill will recognize that, as mentioned above, individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine®, Lysine (K);
5) Isoleucine (I), Leucine (L), Methionine (M), Valine (V); and
6) Phenylalanine (F), Tyrosine (Y), Tryptophan (W).

The phrases "isolated" or "biologically pure" refer to material which is substantially or essentially free from components which normally accompany it as found in its native state. Thus, the peptides described herein do not contain materials normally associated with their in situ environment. Typically, the isolated, antiproliferative peptides described herein are at least about 80% pure, usually at least about 90%, and preferably at least about 95% as measured by band intensity on a silver stained gel.

Protein purity or homogeneity may be indicated by a number of methods well known in the art, such as polyacrylamide gel electrophoresis of a protein sample, followed by visualization upon staining. For certain purposes high resolution will be needed and HPLC or a similar means for purification utilized.

When the antiproliferative peptides are relatively short in length (i.e., less than about 50 amino acids), they are often synthesized using standard chemical peptide synthesis techniques.

Solid phase synthesis in which the C-terminal amino acid of the sequence is attached to an insoluble support followed by sequential addition of the remaining amino acids in the sequence is a preferred method for the chemical synthesis of the antiproliferative peptides described herein. Techniques for solid phase synthesis are known to those skilled in the art.

Alternatively, the antiproliferative peptides described herein are synthesized using recombinant nucleic acid methodology. Generally, this involves creating a nucleic acid sequence that encodes the peptide, placing the nucleic acid in an expression cassette under the control of a particular promoter, expressing the peptide in a host, isolating the expressed peptide or polypeptide and, if required, renaturing the peptide. Techniques sufficient to guide one of skill through such procedures are found in the literature.

Once expressed, recombinant peptides can be purified according to standard procedures, including ammonium sulfate precipitation, affinity columns, column chromatography, gel electrophoresis and the like. Substantially pure compositions of about 50 to 95% homogeneity are preferred, and 80 to 95% or greater homogeneity are most preferred for use as therapeutic agents.

One of skill in the art will recognize that after chemical synthesis, biological expression or purification, the antiproliferative peptides may possess a conformation substantially different than the native conformations of the constituent peptides. In this case, it is often necessary to denature and reduce the antiproliferative peptide and then to cause the peptide to re-fold into the preferred conformation. Methods of reducing and denaturing proteins and inducing re-folding are well known to those of skill in the art.

As employed herein, the phrase "biological activity" refers to the functionality, reactivity, and specificity of compounds that are derived from biological systems or those compounds that are reactive to them, or other compounds that mimic the functionality, reactivity, and specificity of these compounds. Examples of suitable biologically active compounds include enzymes, antibodies, antigens and proteins.

The term "bodily fluid," as used herein, includes, but is not limited to, saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, and vitreal fluid, and nasal secretions.

Important terms that are used herein are defined as follows. "Cancer" means angiogenesis-dependent cancers and tumors, i.e. tumors that require for their growth (expansion in volume and/or mass) an increase in the number and density of the blood vessels supplying them with blood. "Regression" refers to the reduction of tumor mass and size.

As used herein, the term "angiogenesis" and related terms such as "angiogenic" refer to activities associated with blood vessel growth and development, including, but not limited to, endothelial cell proliferation, endothelial cell migration and capillary tube formation.

As used herein, the term "antiangiogenic" refers to compositions and the like that are capable of inhibiting the formation of blood vessels, including but not limited to inhibiting endothelial cell proliferation, endothelial cell migration and capillary tube formation.

Ligands that Bind Components of the Blood Clotting Pathway

The ligands of the present invention bind components of the intrinsic or extrinsic blood coagulation/clotting pathways, including but not limited to, tissue factor (TF), and/or factor V, factor Va, factor VIIa, factor VIII, factor VIIIa, factor IX, factor IXa, factor X, factor Xa, factor XI, factor XIa, factor XII, factor XIIa, thrombin, fibrinogen, fibrin, TF cofactor complexes, factor VIIIa complexes, factor Xa complexes, TF/VIIa complexes, factor Xa/Protein Z complexes, factor Xa/factor Va complexes, factor IXa/factor VIII complexes, factor VIIa multicomplexes, factor Xa multicomplexes, and prothrombinase complexes. Most preferably the ligands of the present invention bind TF, fVIIa, fXa, and/or their multimolecular complexes such as TF/fVIIa complex, prothrombinase complex, fXa/protein Z complex.

Although blood clotting is usually associated with wound healing, it also accompanies a variety of other pathological conditions. The inventors of the present invention have discovered that whereas normal endothelial cells do not synthesize TF, tumor vascular endothelial cells express TF at the onset of tumor angiogenesis. Though not wishing to be bound by the following theory, because TFPI has been shown to inhibit endothelial cell growth (see U.S. patent application Ser. No. 09/130,273, filed Aug. 6, 1998), it is conceivable that, under conditions that promote blood vessel formation, TF mediates the antiproliferative action of TFPI. Since TFPI requires binding to fXa, it is possible that fXa also participates in the transduction of TFPI's antimitotic signal. Moreover, since TF requires fvIIa in order to bind to TFPI/fXIIa, it is also feasible that fVIIa is part of a multimolecular complex that promotes inhibition of angiogenesis. Accordingly, the methods and compositions of the present invention comprise all ligands that bind TF, fVIIa, TFPI/fXIIa, and effect the blood coagulation/clotting pathway by inhibiting angiogenesis.

In addition, the compositions of the present invention further comprise molecules and compounds that effect expression of blood clotting components, and further comprises antibodies and other molecules related to the components. Preferably, the compositions of the present invention include, but are not limited to, proteins comprising Kunitz domain proteins, non-Kunitz domain proteins, Kringle-rich proteins, TF cofactors (i.e. factor VIIa, phospholipids, gangliosides), TF antagonists (i.e. antibodies), and any other molecules that bind TF. More particularly, the compositions of the present invention comprise TFPI, protein S, protein Z, protein Z inhibitor, protein C, activated protein C, protein C inhibitor, prothrombin, group II secretory phospholipase A2, complement protein C4b, protease nexin-1, beta2-glycoprotein I, and serpin anticoagulants (such as antithrombin and particularly heparin cofactor II), and inhibitors of factors TF, TF/VIIa, VIIa, Xa. Most preferably, the compositions of the present invention comprise naturally occurring or synthetic ligands that bind TF.

The ligands of the present invention may be isolated from body fluids including, but not limited to, serum, urine, and ascites, or may be synthesized by chemical or biological methods, such as cell culture, recombinant gene expression, and peptide synthesis. Recombinant techniques include gene amplification from DNA sources using the polymerase chain reaction (PCR), and gene amplification from RNA sources using reverse transcriptase/PCR. LDLR ligands are extracted from body fluids by known protein extraction methods, particularly the method described by Novotny, W. F., et al., *J. Biol. Chem.* 264:18832–18837 (1989).

The inventors of the present invention surprisingly demonstrated the antiproliferative, or more specifically, antiangiogenic properties of the claimed compositions and methods by showing that molecules that bind to components of the blood coagulation/clotting pathway such as TF/factor VIIa complex (i.e., TFPI), or factor Xa (i.e., protein S), inhibit endothelial cell proliferation (see Examples). In addition, the data generated by the inventors demonstrate that binding of a ligand to factor Xa enhances the antiproliferative activity of the ligand (see FIGS. 1B, 2B, 3B, and 4B). Though not wishing to be bound by the following theory, it is believed that in some cases, proteolytic cleavage of the ligand by factor Xa may account for the augmentation of the antiproliferative activity. Indeed, antiangiogenic proteins are often released after a specific cleavage of the parent molecules that possess none or little antiangiogenic activity. For example, plasminogen is cleaved to release ANGIOSTATIN® protein, collagen XVIII is cleaved to release ENDOSTATIN® protein, prolactin is cleaved to release a 16 Kd fragment with potent antiangiogenic properties, while platelet factor-4, a weak inhibitor of angiogenesis, can be cleaved to a fragment that is 50-times more potent than platelet factor-4. Accordingly, as demonstrated by Dr. Folkman, inhibitors of angiogenesis are sometimes "hidden" away as parts of large, abundant but inert molecules that are cleaved to release the antiangiogenic fragments when needed (Hanahan, D., and Folkman, J. Cell 86, 353 (1996)). Blood coagulation often precedes or accompanies formation of new blood vessels (in cases like wound healing or tumor growth), and the inventors of the present invention discovered that blood clotting proteins are cleaved to provide the inhibitors necessary for the regulation of the angiogenic process. Since blood coagulation involves several proteases, one or more of these enzymes (such as factors VIIa and Xa) may participate in the cleavage. For example, factor Xa can cleave prothrombin to release an antiangiogenic fragment.

Accordingly, the present invention further comprises antiangiogenic fragments released by proteolytic cleavage of blood clotting pathway components (i.e., fXa-binding or fXa-mediated proteolytic cleavage, therefore ligands to fXa or proteins that are modified by fXa or another blood coagulation protease such as thrombin are inhibitors of angiogenesis).

Peptides or Protein Fragments

Peptides or protein fragments comprising ligands that bind components of the blood coagulation/clotting pathway, such as TF binding ligands, can be produced from the proteins described above and tested for antiproliferative or antiangiogenic activity using techniques and methods known to those skilled in the art. For example, full length recombinant TFPI (rTFPI) can be produced using the Baculovirus gene expression system. Full length proteins can be cleaved into individual domains or digested using various methods such as, for example, the method described by Enjyoji et al. (*Biochemistry* 34:5725–5735 (1995)). In accordance with the method of Enjyoji et al., rTFPI is treated with a digestion enzyme, human neutrophil elastase, and the digest purified using a heparin column. Human neutrophil elastase cleaves TFPI at Leu$^{89}$ into two fragments: one containing Kunitz-1 and the other containing Kunitz-2 and Kunitz-3. To produce additional fragments, the fragment containing Kunitz-2 and Kunitz-3 (Kunitz-2/Kunitz-3) is preferably treated with a digestion compound, hydroxylamine, according to the method of Balian et al. (*Biochemistry* 11:3798–3806 (1972)), and the digest purified using a heparin column. Hydroxylamine cleaves the fragment containing Kunitz-2 and Kunitz-3 into two fragments: one containing Kunitz-3 and the other containing the Kunitz-2 domain.

Alternatively, fragments are prepared by digesting the entire protein, or large fragments thereof exhibiting antiproliferative activity, to remove one amino acid at a time. Each progressively shorter fragment is then tested for antiproliferative activity. Similarly, fragments of various lengths may be synthesized and tested for anti-proliferative activity. By increasing or decreasing the length of a fragment, one skilled in the art may determine the exact number, identity, and sequence of amino acids within the protein that are required for anti-proliferative activity using routine digestion, synthesis, and screening procedures known to those skilled in the art.

Anti-proliferative activity is evaluated in situ by testing the ability of the fragments to inhibit the proliferation of new blood vessel cells, referred to herein as the inhibition of angiogenesis. A suitable assay is the chick embryo chorioallantoic membrane (CAM) assay described by Crum et al., *Science* 230:1375 (1985) and described in U.S. Pat. No. 5,001,116, which is incorporated by reference herein. The CAM assay is briefly described as follows. Fertilized chick embryos are removed from their shell on day 3 or 4, and a methylcellulose disc containing the fragment of interest is implanted on the chorioallantoic membrane. The embryos are examined 48 hours later and, if a clear avascular zone appears around the methylcellulose disc, the diameter of that zone is measured. The larger the diameter of the zone, the greater the anti-angiogenic activity. Another suitable assay is the HUVEC assay as described in Example 1.

The active fragment is preferably a fragment containing that portion of the ligand that is necessary for binding TF. In particular, ligands having either Kunitz or non-Kunitz domains, or Kringle-rich proteins are preferred. As discussed above, one of skill in the art will recognize that, individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. Accordingly, also included in the present invention are peptides having conservatively modified variations in comparison to the claimed peptides, wherein the chemical reactivity of the peptide is not significantly different from that of the claimed peptide.

Formulations

The naturally occurring or synthetic protein, peptide, or protein fragment, containing all or an active fragment of a ligand that may bind to a component of the blood clotting pathway can be prepared in a physiologically acceptable formulation, such as in a pharmaceutically acceptable carrier, using known techniques. For example, the protein, peptide or protein fragment is combined with a pharmaceutically acceptable excipient to form a therapeutic composition.

Alternatively, the gene for the protein, peptide, or protein fragment, containing all or an active fragment of a desired ligand, may be delivered in a vector for continuous administration using gene therapy techniques. The vector may be administered in a vehicle having specificity for a target site, such as a tumor.

The composition may be in the form of a solid, liquid or aerosol. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection subcutaneously, intravenously, intra-arterially, and formulations for topical and intraocular administration. Examples of aerosol formulations include inhaler formulations for administration to the lungs.

The composition may be administered by standard routes of administration. In general, the composition may be administered by topical, oral, rectal, nasal or parenteral (for example, intravenous, subcutaneous, or intermuscular) routes. In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The dosage of the composition will depend on the condition being treated, the particular composition used, and other clinical factors such as weight and condition of the patient, and the route of administration.

Further, the term "effective amount" refers to the amount of the composition which, when administered to a human or animal, inhibits undesirable cell proliferation, particularly endothelial cell proliferation, causing a reduction in cancer or inhibition in the spread and proliferation of cancer. The effective amount is readily determined by one of skill in the art following routine procedures. For example, antiproliferative compositions of the present invention may be administered parenterally or orally in a range of approximately 1.0 $\mu$g to 1.0 mg per patient, though this range is not intended to be limiting. The actual amount of antiproliferative composition required to elicit an appropriate response will vary for each individual patient depending on the potency of the composition administered and on the response of the individual. Consequently, the specific amount administered to an individual will be determined by routine experimentation and based upon the training and experience of one skilled in the art.

The composition may be administered in combination with other compositions and procedures for the treatment of diseases. For example, unwanted cell proliferation may be treated conventionally with surgery, radiation or chemotherapy in combination with the administration of the composition, and additional doses of the composition may be subsequently administered to the patient to stabilize and inhibit the growth of any residual unwanted cell proliferation.

Antibodies of Ligands that Bind Blood Clotting Components

The present invention further comprises antibodies of ligands that bind blood coagulation/clotting components that may be used for diagnostic as well as therapeutic purposes. The antibodies provided herein are monoclonal or polyclonal antibodies having binding specificity for desired ligands. The preferred antibodies are monoclonal antibodies, due to their higher specificity for the ligands. The antibodies exhibit minimal or no crossreactivity with other proteins or peptides. Preferably, the antibodies are specific for ligands comprising Kunitz domain proteins, non-Kunitz domain proteins, Kringle-rich proteins, TF cofactors (i.e. factor V, factor VIIa, factor Xa, phospholipids, gangliosides), TF antagonists (i.e. antibodies), and any other molecules that bind TF including but not limited to sPLA2, APC, anticoagulant protein S, tick anticoagulant peptide, TFPI, thrombin and antithrombin. Most preferably the antibodies are specific for TF ligands.

Monoclonal antibodies are prepared by immunizing an animal, such as a mouse or rabbit, with a whole or immunogenic portion of a desired ligand, such as antithrombin III. Spleen cells are harvested from the immunized animals and hybridomas generated by fusing sensitized spleen cells with a myeloma cell line, such as murine SP2/O myeloma cells (ATCC, Manassas, Va.). The cells are induced to fuse by the addition of polyethylene glycol. Hybridomas are chemically selected by plating the cells in a selection medium containing hypoxanthine, aminopterin and thymidine (HAT).

Hybridomas are subsequently screened for the ability to produce monoclonal antibodies against ligands. Hybridomas producing antibodies that bind to the ligands are cloned, expanded and stored frozen for future production. The preferred hybridoma produces a monoclonal antibody having the IgG isotype, more preferably the IgG1 isotype.

The polyclonal antibodies are prepared by immunizing animals, such as mice or rabbits with a ligand such as antithrombin as described above. Blood sera is subsequently collected from the animals, and antibodies in the sera screened for binding reactivity against the ligand, preferably the antigens that are reactive with the monoclonal antibody described above.

Either the monoclonal antibodies or the polyclonal antibodies, or both may be labeled directly with a detectable label for identification and quantitation of ligands in a biological as described below. Labels for use in immunoassays are generally known to those skilled in the art and include enzymes, radioisotopes, and fluorescent, luminescent and chromogenic substances including colored particles, such as colloidal gold and latex beads. The antibodies may also be bound to a solid phase to facilitate separation of antibody-antigen complexes from non-reacted components in an immunoassay. Exemplary solid phase substances include, but are not limited to, microtiter plates, test tubes, magnetic, plastic or glass beads and slides. Methods for coupling antibodies to solid phases are well known to those skilled in the art.

Alternatively, the antibodies may be labeled indirectly by reaction with labeled substances that have an affinity for immunoglobulin, such as protein A or G or second antibodies. The antibodies may be conjugated with a second substance and detected with a labeled third substance having an affinity for the second substance conjugated to the antibody. For example, the antibodies may be conjugated to biotin and the antibody-biotin conjugate detected using labeled avidin or streptavidin. Similarly, the antibodies may be conjugated to a hapten and the antibody-hapten conjugate detected using labeled anti-hapten antibody. These and other methods of labeling antibodies and assay conjugates are well known to those skilled in the art.

Sensitive immunoassays employing one or more of the antibodies described above are provided by the present invention. The immunoassays are useful for detecting the presence or amount of ligands in a variety of samples, particularly biological samples, such as human or animal biological fluids. The samples may be obtained from any source in which the ligands may exist. For example, the sample may include, but is not limited to, blood, saliva, semen, tears, and urine.

The antibody-antigen complexes formed in the immunoassays of the present invention are detected using immunoassay methods known to those skilled in the art, including sandwich immunoassays and competitive immunoassays. The antibody-antigen complexes are exposed to antibodies similar to those used to capture the antigen, but which have been labeled with a detectable label. Suitable labels include: chemiluminescent labels, such as horseradish peroxidase; electrochemiluminescent labels, such as ruthenium and aequorin; bioluminescent labels, such as luciferase; fluorescent labels such as FITC; and enzymatic labels such as alkaline phosphatase, β-galactosidase, and horseradish peroxidase.

The labeled complex is then detected using a detection technique or instrument specific for detection of the label employed. Soluble antigen or antigens may also be incubated with magnetic beads coated with non-specific antibodies in an identical assay format to determine the background values of samples analyzed in the assay.

Pharmaceutical Compositions

The compositions of the present invention are useful in therapeutic and prophylactic applications for the treatment of diseases mediated by undesirable cell proliferation such as cancer.

As such, the present invention provides pharmaceutical compositions wherein the compositions generally comprise one more ligands, or active fragments thereof that bind components of the blood clotting pathway together with a pharmaceutically acceptable carrier. Such compositions are suitable for use in a variety of drug delivery systems. Suitable formulations for use in the present invention are found in *Remington's Pharmaceutical Sciences*, Mack Publishing Company, Philadelphia, Pa., 17th ed. (1985), which is incorporated herein by reference. For a brief review of methods for drug delivery, see, Langer, *Science* 249:1 527–1533 (1990), which is incorporated herein by reference.

The pharmaceutical compositions of the invention are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration that comprise a solution of the agents described above dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, the polypeptides are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

The amount administered to the patient will vary depending upon what is being administered, the state of the patient and the manner of administration. In therapeutic applications, compositions are administered to a patient already suffering from a disease mediated by undesirable cell proliferation, in an amount sufficient to inhibit cell proliferation, or at least partially arrest the symptoms of the disease and its complications. An amount adequate to accomplish this is defined as "therapeutically effective dose." Amounts effective for this use will depend on the severity of the disease, the particular composition, and the weight and general state of the patient. Generally, the dose will be in the range of about 0.5 mg to about 5 mg per day, preferably about 100 mg per day, for a 70 kg patient.

In a preferred embodiment, the ligands, or active fragments thereof that bind components of the blood clotting pathway are covalently attached (conjugated) to a carrier protein as described above. Useful carrier proteins include, but are not limited to, thyroglobulin, albumins such as human serum albumin, tetanus toxoid, polyamino acids such as poly(D-lysine:D-glutamic acid), influenza. The compositions can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art.

In addition, DNA or RNA encoding the ligands, or active fragments thereof, that bind components of the blood clotting pathway may be introduced into patients to obtain an immune response to the immunogenic peptides which the nucleic acid encodes. See, Wolff, et al., *Science* 247: 1465–1468 (1990) which describes the use of nucleic acids to produce expression of the ligands which the nucleic acids encode, the teachings of which are incorporated herein by reference.

Diseases and Conditions to be Treated

The methods and compositions described herein are useful for treating human and animal diseases and processes mediated by abnormal or undesirable cellular proliferation, particularly abnormal or undesirable endothelial cell proliferation, including, but not limited to, hemangioma, solid tumors, leukemia, metastasis, telangiectasia psoriasis scleroderma, pyogenic granuloma, myocardial angiogenesis, plaque neovascularization, coronary collaterals, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, and placentation. The method and composition are particularly useful for treating angiogenesis-related disorders and diseases by inhibiting angiogenesis.

The methods and compositions described herein are particularly useful for treating cancer, arthritis, macular degeneration, and diabetic retinopathy. Administration of the compositions to a human or animal having prevascularized metastasized tumors is useful for preventing the growth or expansion of such tumors.

The compositions and methods are further illustrated by the following non-limiting examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Inhibition of Human Umbilical Vascular Endothelial Cell Proliferation by TFPI and Factor Xa Human Umbilical Vascular Endothelial Cell Proliferation Assay Human umbilical vascular endothelial cells (HUVECs) and their media (EGM and EBM) were purchased from Clonetics (San Diego, Calif.).

HUVECs were routinely cultured to confluency in EGM. The cells were trypsinized and plated in a 96-well plate at 5,000 cells per 100 $\mu$l EBM supplemented with 2% serum and antibiotics. The cells were allowed to adhere to the plate for at least 2 hrs. Then, bFGF at 10 ng/ml and various concentrations of an antiangiogenic agent were added to the wells. The cells were cultured for 48 hrs at 37° C. in a 5% $CO_2$ atmosphere. Cell proliferation was determined using a uridine incorporation method (Boehringer Mannheim Corporation, Indianapolis, Ind.).

As shown in FIG. 1A, TFPI inhibits bFGF-induced proliferation of HUVEC cells. Preincubation of 0.028 $\mu$M and 0.139 $\mu$M TFPI with factor Xa (fXa) in the presence of phospholipids led to an increased antiproliferative activity of these two concentrations of TFPI (FIG. 1B). SDS-PAGE mobility/Immunoblotting of the mixture TFPI/factor Xa/phospholipids revealed that fXa partially cleaved TFPI to fragments with approximate MW 30 Kd and 20 Kd (FIG. 1C).

Based on the findings of this experiment, it is likely that complexing with factor Xa and/or fragmentation of TFPI may enhance the antiangiogenic activity of TFPI.

EXAMPLE 2

Figure 2C:
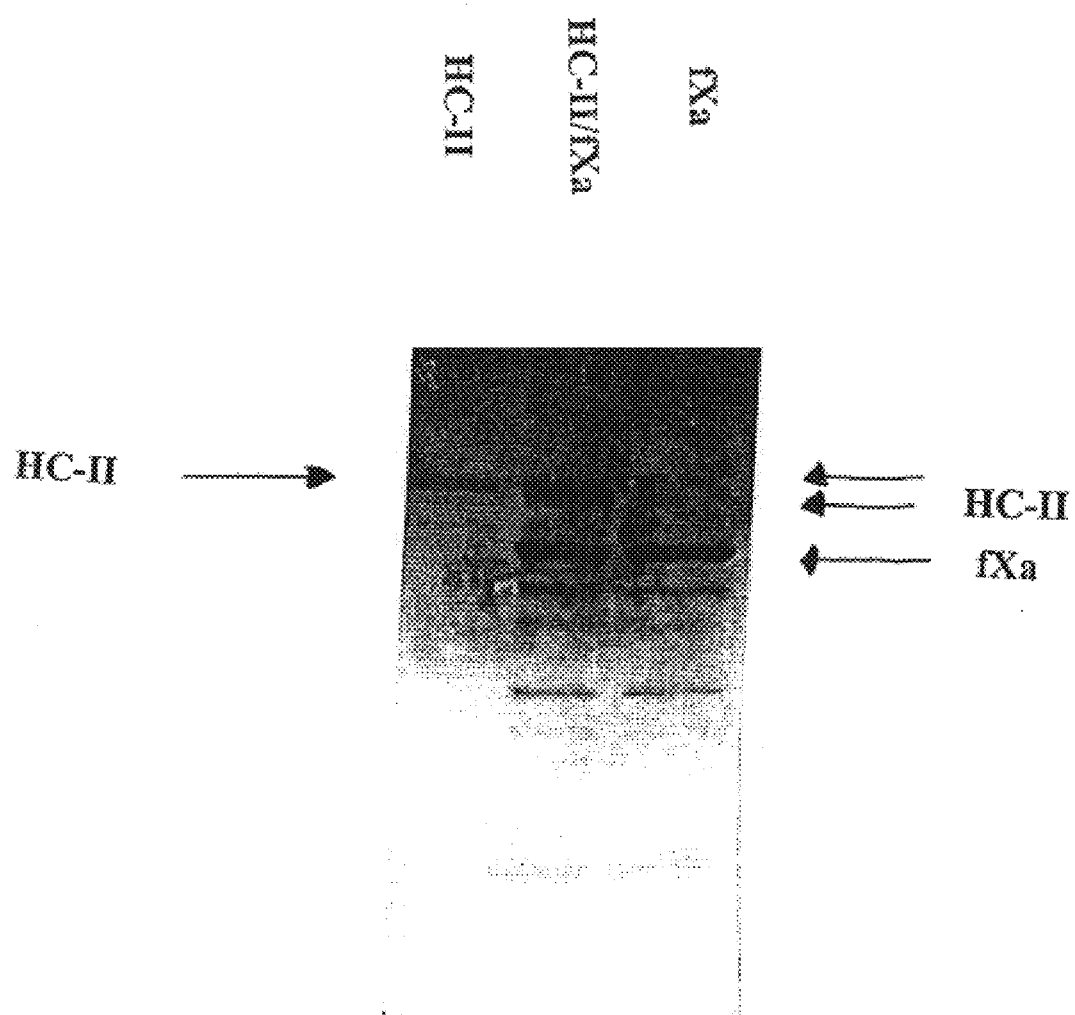
FIG. 2C is a representation of the results of an SDS-PAGE mobility analysis of the mixture HC-II/factor Xa/phospholipids showing that though there is no significant cleavage of HC-II, cleavage of a limited number of amino acid residues from either N- or C-terminal of the protein is possible.

Inhibition of Human Umbilical Vascular Endothelial Cell Proliferation by Heparin Cofactor II Using a HUVEC assay as described above in Example 1, it was demonstrated that Heparin Cofactor II (HC-II) inhibits bFGF-induced proliferation of HUVEC cells (FIG. 2A). Preincubation of 0.6 $\mu$M HC-II with fXa in the presence of phospholipids led to an increased antiproliferative activity (FIG. 2B). SDS-PAGE mobility of the mixture HC-II/factor Xa/phospholipids did not reveal any significant cleavage of HC-II, although cleavage of a limited number of amino acid residues from either N- or C-terminal of the protein is possible, especially since there is a slight down-shift of the HC-II band after incubation with fXa (FIG. 2C).

Based on the findings of this experiment, it is likely that complexing HC-II with factor Xa and/or proteolytic cleavage of limited number of residues of HC-II enhances the antiangiogenic activity of HC-II.

EXAMPLE 3

Figure 3A:
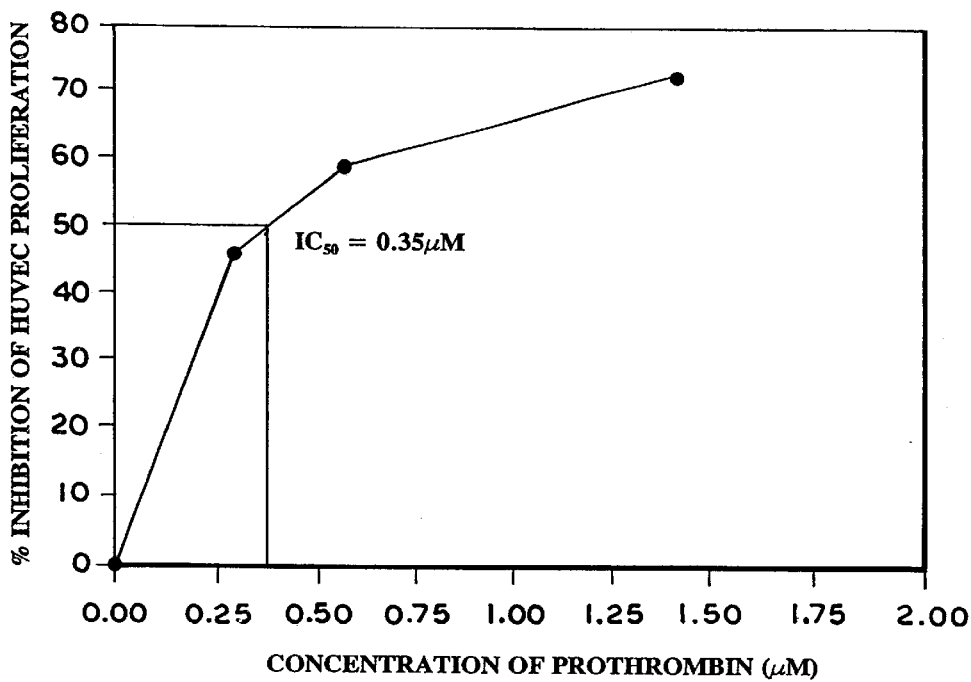
FIG. 3A is a graph showing inhibition of bFGF-induced proliferation of HUVEC cells by Prothrombin (Pro).
Figure 3B:
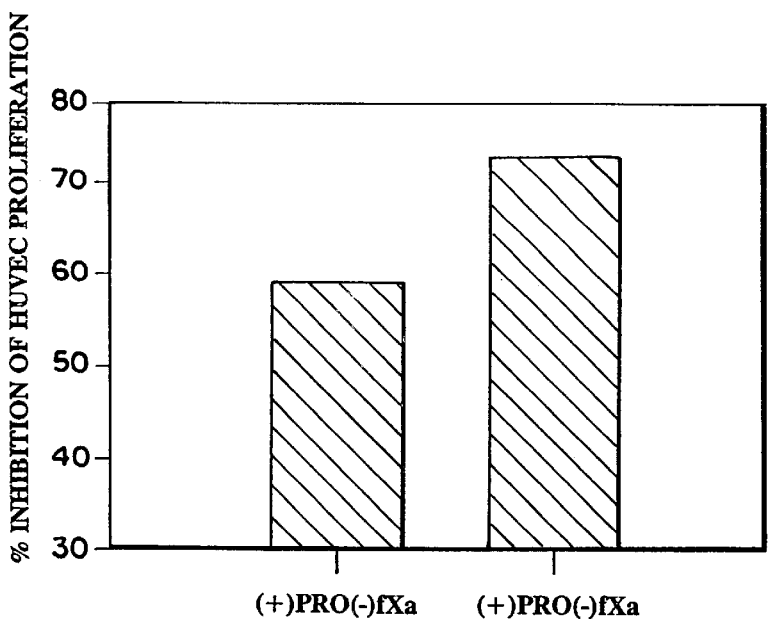
FIG. 3B is a graph showing increased antiproliferative activity of HC-II following preincubation of 0.55 μM Pro with fXa in the presence of phospholipids.
Figure 3C:
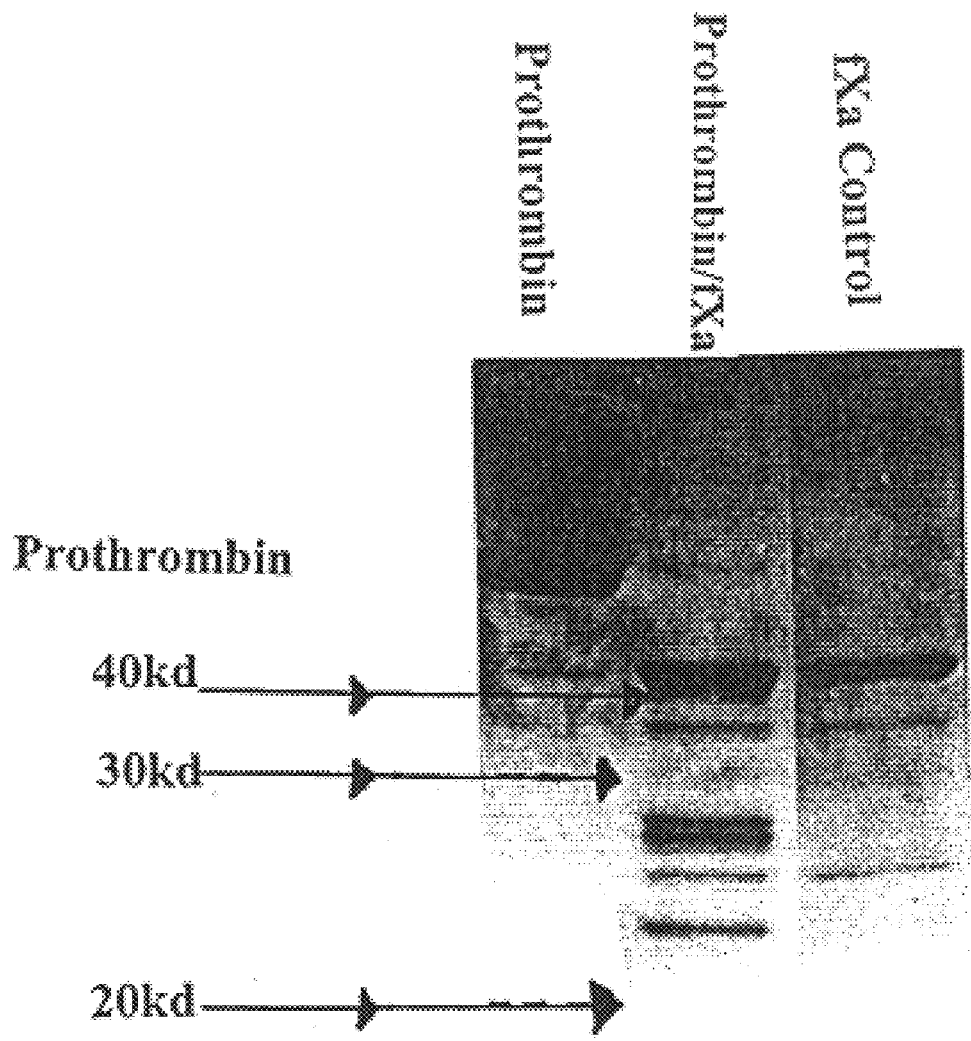
FIG. 3C is a representation of the results of an SDS-PAGE mobility analysis of the mixture of Pro/factor Xa/phospholipids revealing complete fragmentation of Pro into three fragments with approximate MW of 40, 30, and 14 Kd.

Inhibition of Human Umbilical Vascular Endothelial Cell Proliferation by Prothrombin Using a HUVEC assay as described above in Example 1, it was demonstrated that Prothrombin (Pro) inhibits bFGF-induced proliferation of HUVEC cells (FIG. 3A). Preincubation of 0.55 $\mu$M Pro with fXa in the presence of phospholipids led to an increased antiproliferative activity (FIG. 2B). SDS-PAGE mobility of the mixture Pro/factor Xa/phospholipids revealed complete fragmentation of Pro into three fragments with approximate MW of 40, 30, and 14 Kd (FIG. 3C).

Based on the findings of this experiment, it is likely that complexing prothrombin with factor Xa enhances the antiangiogenic activity of prothrombin.

EXAMPLE 4

Figure 4C:
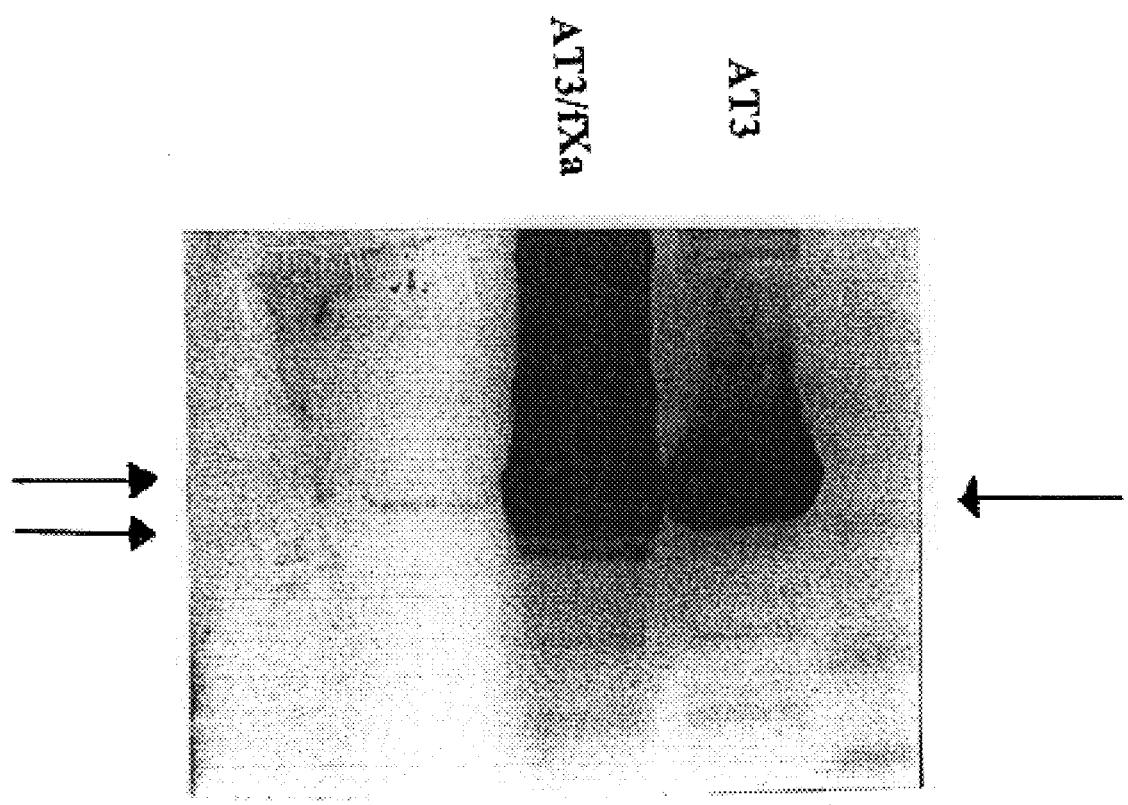
FIG. 4C is a representation of the results of an SDS-PAGE mobility analysis of the mixture of AT3-II/factor Xa/phospholipids revealing minor cleavage of AT3.

Inhibition of Human Umbilical Vascular Endothelial Cell Proliferation by Antithrombin III Using a HUVEC assay as described above in Example 1, it was demonstrated that Antithrombin III (AT3) inhibits bFGF-induced proliferation of HUVEC cells (FIG. 4A). Preincubation of 0.6 mM AT3 with fXa in the presence of phospholipids led to an increased antiproliferative activity (FIG. 4B). SDS-PAGE mobility/Immunoblotting of the mixture AT3-II/factor Xa/phospholipids revealed minor cleavage of AT3 (FIG. 4C).

Based on the findings of this experiment, it is likely that complexing with factor Xa and/or proteolytic cleavage of limited number of residues of AT3 may enhance the antiangiogenic activity of AT3.

EXAMPLE 5

Figure 5:
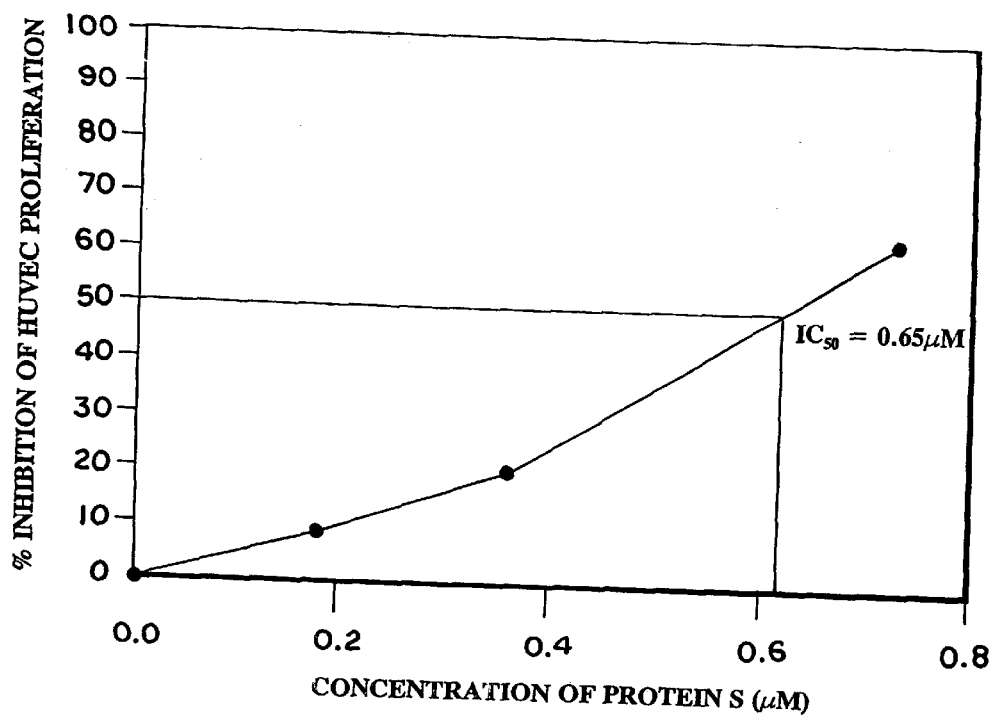
FIG. 5 is a graph showing inhibition of bFGF-induced proliferation of HUVEC cells by Protein S.

Inhibition of Human Umbilical Vascular Endothelial Cell Proliferation by Antithrombin III Using a HUVEC assay as described above in Example 1, it was demonstrated that Protein S inhibits bFGF-induced proliferation of HUVEC cells (FIG. 5).

We claim:

1. A method of treating a human or animal having undesirable endothelial cell proliferation comprising,
   administering to the human or animal an effective amount of a composition comprising
   a) an isolated protein or peptide, or active fragment thereof, wherein the protein or peptide comprises a ligand, wherein the ligand binds to one or more components of the blood clotting pathway, and wherein the active fragment of the isolated protein or peptide binds to one or more components of the blood clotting pathway; and b) a pharmaceutically acceptable excipient, carrier or sustained-release matrix, wherein the effective amount is sufficient to inhibit the undesirable cell proliferation.

2. The method of claim 1, wherein the components of the blood clotting pathway are selected from the group consisting of tissue factor, factor V, factor Va, factor VIIa, factor VIII, factor VIIIa, factor IX, factor IXa, factor X, factor Xa, factor XI, factor XIa, factor XII, factor XIIa, thrombin, fibrinogen, fibrin, a TF cofactor complex, a factor VIIIa complex, a factor Xa complex, a factor TF/VIIIa complex, a factor Xa/Protein Z complex, a factor Xa/factor Va complex, a factor IXa/factor VIII complex, a factor VIIa multicomplex, a factor Xa multicomplex, and a prothrombinase complex.

3. The method of claim 1, wherein the ligand is selected from the group consisting of Kunitz domain proteins, non-Kunitz domain proteins, Kringle-rich proteins, TF cofactors, TF antagonists, TF antibodies, and active fragments thereof, wherein the active fragments bind to one or more components of the blood clotting pathway.

4. The method of claim 3, wherein the TF cofactors are selected from the group consisting of factor VIIa, phospholipids, and gangliosides.

5. The method of claim 1, wherein the isolated protein or peptide comprises a ligand selected from the group consisting of TFPI, antithrombin III, prothrombin, heparin cofactor II, anticoagulant protein, protein C, activated protein C, protein C inhibitor, protein S, protein Z, protein Z inhibitor, tick anticoagulant peptide, protease nexin-1, beta2-glycoprotein I, complement protein C4b, and group II secretory phospholipase A2.

6. The method of claim 5, wherein the ligand is selected from the group consisting of thrombin, prothrombin, and antithrombin III.

7. The method of claim 1, wherein the undesirable cell proliferation is undesirable endothelial cell proliferation.

8. The method of claim 7 wherein the inhibition of endothelial cell proliferation inhibits neovascularization.

9. The method of claim 1, wherein the undesirable cell proliferation is an angiogenesis-related disease.

10. The method of claim 9, wherein the angiogenic-related disease is a disease selected from the group consisting of cancer, arthritis, macular degeneration, and diabetic retinopathy.

11. A method of treating undesirable angiogenesis in a human or animal comprising administering to the human or animal a composition comprising an effective amount of an angiogenesis-inhibiting ligand wherein the ligand binds to one or more components of the blood clotting pathway, and a pharmaceutically acceptable excipient, carrier or sustained-release matrix.

12. The method of claim 11, wherein the components of the blood clotting pathway are selected from the group consisting of tissue factor, factor V, factor Va, factor VIIa, factor VIII, factor VIIIa, factor IX, factor IXa, factor X, factor Xa, factor XI, factor XIa, factor XII, factor XIIa, thrombin, fibrinogen, fibrin, a TF cofactor complex, a factor VIIIa complex, a factor Xa complex, a factor TF/VIIIa complex, a factor Xa/Protein Z complex, a factor Xa/factor Va complex, a factor IXa/factor VIII complex, a factor VIIa multicomplex, a factor Xa multicomplex, and prothrombinase complex.

13. The method of claim 11, wherein the ligand is selected from the group consisting of Kunitz domain proteins, non-Kunitz domain proteins, Kringle-rich proteins, TF cofactors, TF antagonists, TF antibodies, and active fragments thereof, wherein the active fragments bind to one or more components of the blood clotting pathway.

14. The method of claim 13, wherein the ligand is selected from the group consisting of TFPI, antithrombin III, prothrombin, heparin, cofactor II, anticoagulant protein, protein C, activated protein C, protein C inhibitor, protein S, protein Z, protein Z inhibitor, tick anticoagulant peptide, protease nexin-1, beta2-glycoprotein I, complement protein C4b, and group II secratory phospholipase A2.

15. The method of claim 13, wherein the undesired angiogenesis is an angiogenic-related disease selected from the group consisting of cancer, arthritis, macular degeneration, and diabetic retinopathy.

16. A compound for treating undesired angiogenesis in a human or animal comprising an effective amount of an angiogenesis-inhibiting ligand, or active fragment thereof, wherein the ligand binds to one or more components of the blood clotting pathway and wherein the active fragment binds to one or more components of the blood clotting pathway.

17. The compound of claim 16, wherein the components of the blood clotting pathway are selected from the group consisting of tissue factor, factor V, factor Va, factor VIIa, factor VIII, factor VIIIa, factor IX, factor IXa, factor X, factor Xa, factor XI, factor XIa, factor XII, factor XIIa, thrombin, fibrinogen, fibrin, a TF cofactor complex, a factor VIIIa complex, a factor Xa complex, a factor TF/VIIIa complex, a factor Xa/Protein Z complex, a factor Xa/factor Va complex, a factor IXa/factor VIII complex, a factor VIIa multicomplex, a factor Xa multicomplex, and a prothrombinase complex.

18. The compound of claim 16, wherein the ligand is selected from the group consisting of Kunitz domain proteins, non-Kunitz domain proteins, Kringle-rich proteins, TF cofactors, TF antagonists, TF antibodies, and active fragments thereof, wherein the active fragments bind to one or more components of the blood clotting pathway.

19. The compound of claim 16, wherein the ligand is selected from the group consisting of antithrombin III, tissue factor pathway inhibitor and active fragments thereof, wherein the active fragments bind to one or more components of the blood clotting pathway.

20. A composition comprising the compound of claim 16 and a pharmaceutically acceptable excipient, carrier or sustained-release matrix.

21. The compound of claim 16 wherein the undesired angiogenesis is an angiogenesis-related disease.

22. The compound of claim 16 wherein the angiogenic-related disease is selected from the group consisting of cancer, arthritis, macular degeneration, and diabetic retinopathy.

* * * * *